(12) United States Patent
Hohman

(10) Patent No.: US 10,568,934 B2
(45) Date of Patent: Feb. 25, 2020

(54) METHOD OF TREATING AMD IN PATIENTS REFRACTORY TO ANTI-VEGF THERAPY

(71) Applicant: Allergan, Inc., Irvine, CA (US)

(72) Inventor: Thomas Conlon Hohman, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/887,555

(22) Filed: May 6, 2013

(65) Prior Publication Data

US 2013/0296238 A1 Nov. 7, 2013

Related U.S. Application Data

(60) Provisional application No. 61/643,878, filed on May 7, 2012, provisional application No. 61/728,017, filed on Nov. 19, 2012, provisional application No. 61/731,238, filed on Nov. 29, 2012.

(51) Int. Cl.
*A61K 38/17* (2006.01)
*A61K 47/60* (2017.01)

(52) U.S. Cl.
CPC ............ *A61K 38/177* (2013.01); *A61K 47/60* (2017.08)

(58) Field of Classification Search
CPC .............. A61K 39/1709; A61K 38/177; A61K 14/4703; A61K 9/0048
See application file for complete search history.

(56) References Cited

U.S. PATENT DOCUMENTS

| | | | |
|---|---|---|---|
| 6,365,569 B1 | 4/2002 | Tang et al. | |
| 6,485,935 B1 | 11/2002 | Morrow et al. | |
| 7,417,130 B2 | 8/2008 | Stumpp et al. | |
| 8,110,653 B2 | 2/2012 | Stumpp et al. | |
| 8,710,187 B2 | 4/2014 | Binz et al. | |
| 8,901,076 B2 | 12/2014 | Binz et al. | |
| 2002/0022258 A1 | 2/2002 | Song et al. | |
| 2002/0042094 A1 | 4/2002 | Venezia et al. | |
| 2006/0121045 A1 | 6/2006 | Iverson et al. | |
| 2013/0296238 A1 | 11/2013 | Hohman | |
| 2014/0005125 A1 | 1/2014 | Baumann | |
| 2015/0126458 A1 | 5/2015 | Hohman et al. | |

FOREIGN PATENT DOCUMENTS

| | | |
|---|---|---|
| WO | WO 96/06166 | 2/1996 |
| WO | WO 98/06845 | 2/1998 |
| WO | WO 00/34784 | 6/2000 |
| WO | WO 00/75319 | 12/2000 |
| WO | WO 01/61005 | 8/2001 |
| WO | WO 01/85909 | 11/2001 |
| WO | WO 02/20565 | 3/2002 |
| WO | WO 2005/056764 | 6/2005 |
| WO | WO 2007/080392 | 7/2007 |
| WO | WO 2007/103515 | 9/2007 |
| WO | WO 2008/066752 | 6/2008 |
| WO | WO 2008/097497 | 8/2008 |
| WO | WO 2008/155134 | 12/2008 |
| WO | WO 2009/115919 | 9/2009 |
| WO | WO 2010/060748 | 6/2010 |
| WO | WO 2011/135067 | 11/2011 |
| WO | WO 2012/069655 | 5/2012 |

OTHER PUBLICATIONS

Wolf et al. "Phase I Mp0112 Wet AMD Study: Results of a Single Escalating Dose Study With DARPin® MP0112 in Wet AMD" ARVO 2011 Visionary Genomics, May 1-5, 2011, Fort Lauderdale, FL, Abstract for Presentation/Poster # 165 conducted May 2, 2011.*
Molecular Partners "DARPin Technology, A Robust Platform for the Generation of Novel Therapeutic Proteins," Apr. 2010 dowloaded from http://www.biotechday.ch/media/biotechday/downloads/molecularpartners.pdf on Jan. 31, 2014.*
Cohen "Anti-VEGF drugs as the 2003 first-line therapy for choroidal neovascularization in pathologic myopia," The Journal of Retinal and Vitreous Diseases, 2009, vol. 29, No. 8, pp. 1062-1066.*
Iturralde et al. "Intravitreal bevacizumab (avastin) treatment of macular edema in central retinal vein occlusion," The Journal of Retinal and Vitreous Diseases, 2006, vol. 26, No. 3, pp. 279-284.*
Campochiaro et al. "Ranibizumab for Macular Edema following Branch Retinal Vein Occlusion" Opthalmology, 2010, vol. 117, No. 6, pp. 1102-1112.*
Papadopoulos et al. "Binding and neutralization of vascular endothelial growth factor (VEGF) and related ligands by VEGF Trap, ranibizumab and bevacizumab," Angiogenesis (2012) 15:171-185.*
Krohne et al. "Intraocular Pharmacokinetics of Bevacizumab After a Single Intravitreal Injection in Humans" American Jounral of Ophthalmology, Oct. 2008, pp. 508-512.*
Keane et al. "Development of Anti-VEGF Therapies for Intraocular Use: A Guide for Clinicians," Journal of Ophthalmology vol. 2012, Article ID 483034, pp. 1-13.*
Slakter "What to do When AntiVEGF Therapy 'Fails'" Retinal Physician, Jun. 1, 2010, pp. 1-10.*
Almony et al. "Efficacy of intravitreal bevacizumab after unresponsive treatment with intravitreal ranibizumab," Can J Ophthalmol 2011;46:182-5.*
Clincial Trial NCT01543568, updated Mar. 2, 2012, downloaded from www.clinicaltrials.gov on Jun. 25, 2017.*
Ohr and Kaiser ("Aflibercept in wet age-related macular degeneration: a perspective review," Ther Adv Chronic Dis (2012) 3(4) 153-161, first published Apr. 27, 2012) (Year: 2012).*

(Continued)

*Primary Examiner* — Christina Bradley
(74) *Attorney, Agent, or Firm* — Michael T. Barber

(57) ABSTRACT

Disclosed herein are methods for the treatment of a patient having an ocular conditions such as age-related macular degeneration or diabetic macular edema through administration of a recombinant binding protein comprising an ankyrin repeat domain. In some embodiments, the composition may be administered every 8 weeks to every 16 weeks. In some embodiments, the patient being treated may be refractory to existing anti-VEGF therapies.

6 Claims, 4 Drawing Sheets
Specification includes a Sequence Listing.

(56) References Cited

OTHER PUBLICATIONS

Sheybani et al. ("Anti-VEGF Non-Responders in Neovascular AMD," Review of Opthamology, Mar. 19, 2010, downloaded from www.reviewofophthalmology.com) (Year: 2010).*
Weiner et al. ("When Anti-VEGF Fails in AMD Patients: 3 Treatment Approaches," Eyenet Magazine, May 2012, pp. 37-39) (Year: 2012).*
Stahl et al, "Highly potent VEGF-A-antagonistic DARPins as anti-angiogenic agents for topical and intravitreal applications", Sep. 15, 2012, vol. 16, No. 1, pp. 101-111.
International Search Report, Mailed Jul. 10, 2013, International Application No. PCT/US2013/039619.
Binz et al., "High-affinity binders selected from designed ankyrin repeat protein libraries", Nature Biotechnology, vol. 22, No. 5, May 1, 2004, pp. 575-582.
Binz et al., "Engineering novel binding proteins from nonimmunoglobulin domains", Nature Biotechnololgy, 23, 2005, pp. 1257-1268.
Eugene et al, "Anti-VEGF aptamer (pegaptanib) therapy for ocular vascular diseases", Annals of the New York Academy of Sciences, Jan. 1, 2006, pp. 151-171.
Forrer et al, "Consensus design of repeat proteins", Chembiochem-A Europen Journal of Chemical Biology, vol. 5, No. 2, Feb. 6, 2004, pp. 183-189.
Inoki et al, "Connective tissue growth factor binds vascular endothelial growth factor (VEGF) and inhibits VEGF-induced angiogenesis", The FASEB Journal, vol. 16., No. 2, Feb. 2002, pp. 219-221.
Kajava et al, "Structural Diversity of Leucine-Rich Repeat Proteins", Journal of Molecular Biology, vol. 277, No. 277, 1998, pp. 519-527.
Kobe et al, "A structural basis of the interactions between leucine-rich repeats and protein ligands", Nature, vol. 374, Mar. 9, 1995, pp. 183-186.
Konopatskaya et al., "VEGF$_{165}$b, an endogenous C-terminal splice variant of VEGF, inhibits retinal neovascularization in mice", Molecular Vision 12, 2006, pp. 626-632.
Korff et al., << Integration of Endothelial Cells in Multicellular Spheroids Prevents Apoptosis and Induces Differentiation >>, J. Cell Biol. 143(5), 1341-1352, 1998)
Nygren et al, "Scaffolds for engineering novel binding sites in proteins", Current Opinion in Structural Biology, vol. 7, No. 4, 1997, pp. 463-469.
Sassa et al, << Antiangiogenic drugs in the management of ocular diseases : Focus on antivascular endothelial growth factor >>, Clinical Ophthalmology, vol. 4, No. 1, Apr. 26, 2010, pp. 275-283.
Sedgwick et al, "The ankyrin repeat: a diversity of interactions on a common structural framework", TIBS Trends in Biochemical Sciences, vol. 24, No. 8, Aug. 1, 1999, pp. 311-316.
Skerra, "Engineered protein scaffolds for molecular recognition", J. Mol. Recog., 13, 2000, pp. 167-187.
Stumpp et al, "DARPins: A new generation of protein therapeutics", Drug Discovery Today, vol. 13, No. 15-16, Aug. 1, 2008, pp. 695-701.
Vance et al, "The design of polyvalent scaffolds for targeted delivery", Advanced Drug Delivery Reviews, vol. 61, No. 11, Sep. 30, 2009, pp. 931-939.
Zhang et al, "A minimum folding unit in the ankyrin repeate protein p16INK4", Journal of Molecular Biology vol. 299, No. 4, 2000, pp. 1121-1132.
Berendsen, A Glimpse of the Holy Grail?, Science, 1998, 642-643, 282.
Bradley et al, Limits of Cooperativity in a Structurally Modular Protein: Response of the Notch Ankyrin Domain to Analogous Alanine Substitutions in Each Repeat., J. Mol. Biol., 2002, 373-386, 324.
Definition of moiety, from http://dictionary.reference.com/browse/moiety, Definition of moiety, accessed Aug. 26, 2010, pp. 1-3.
Lu et al., Effect of PEGylation on the Solution Conformation of Antibody Fragments, Journal of Pharmaceutical Sciences, 2008, 2062-2079, 97.
Ng, Eugene W. M. et al., Anti-VEGF aptamer (pegaptanib) therapy for ocular vascular diseases, Annals of the New York Academy of Sciences, New York Academy of Sciences, New York, NY, Jan. 1, 2006, 151-171.
Ngo Et Al., Computational Complexity, Protein Structure Protection, and the Levinthal Paradox, In Merz and Le Grand (Eds.) The Protein Folding Problem and Tertiary Structure Prediction., 1994, 491-495, Birkhauser:Boston.
Rudinger, Peptide Hormones, JA Parsons, Ed., 1976, pp. 1-7.
Voet et al., Biochemistry, John Wiley & Sons Inc., 1995, pp. 235-241.
Wells, J.A., Additivity of mutational effects in proteins., Biochemistry, 1990, 8509-8517, 29(37).
Williamson Eye Institute, Age-Related Macular Degeneration, 2010 downloaded from http://www. williamsoneyeinstitute.com/other-eye-disorders/macular-degeneration on Feb. 20, 2015.
Zahnd et al., A Designed Ankyrin Repeat Protein Evolved to Picomolar Affinity to Her2, J. Mol. Bio., 2007, pp. 1015-1028, 369.

* cited by examiner

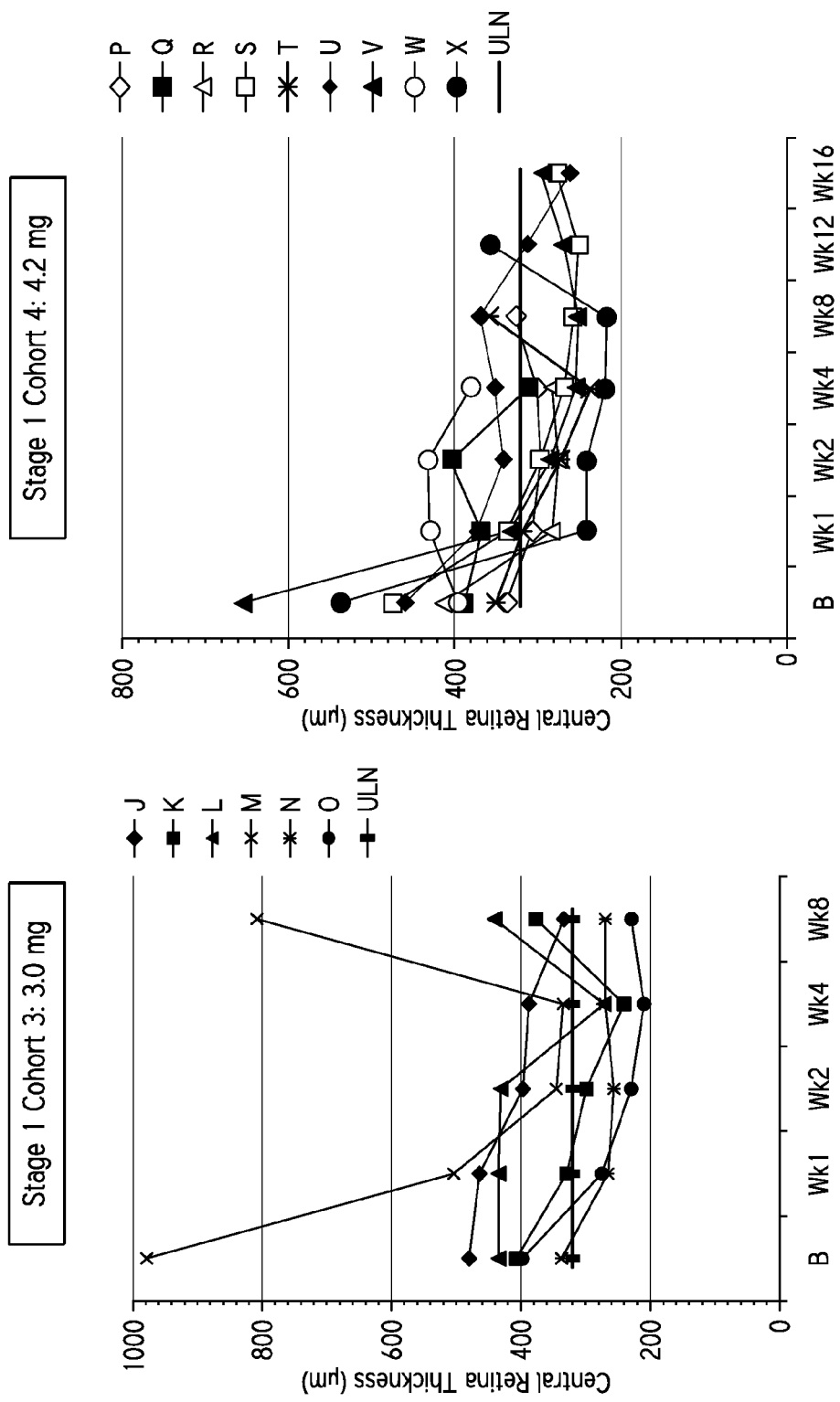

SEQUENCE LISTING

```
<160> NUMBER OF SEQ ID NOS: 9

<210> SEQ ID NO 1
<211> LENGTH: 1025
<212> TYPE: PRT
<213> ORGANISM: Artificial Sequence
<220> FEATURE:
<223> OTHER INFORMATION: Ankyrin repeat protein

<400> SEQUENCE: 1

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Ala Asp
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110

Leu Gly Arg Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140
```

-continued

Asp Asn Gly Asn Glu Asp Leu Ala Glu Ile Leu Gln Lys Ala Ala Ser
145                 150                 155                 160

Gly Ser Pro Ala Gly Ser Pro Thr Ser Thr Glu Glu Gly Thr Ser Glu
                165                 170                 175

Ser Ala Thr Pro Glu Ser Gly Pro Gly Thr Ser Thr Glu Pro Ser Glu
            180                 185                 190

Gly Ser Ala Pro Gly Ser Pro Ala Gly Ser Pro Thr Ser Thr Glu Glu
            195                 200                 205

Gly Thr Ser Thr Glu Pro Ser Glu Gly Ser Ala Pro Gly Thr Ser Thr
        210                 215                 220

Glu Pro Ser Glu Gly Ser Ala Pro Gly Thr Ser Glu Ser Ala Thr Pro
225                 230                 235                 240

Glu Ser Gly Pro Gly Ser Glu Pro Ala Thr Ser Gly Ser Glu Thr Pro
                245                 250                 255

Gly Ser Glu Pro Ala Thr Ser Gly Ser Glu Thr Pro Gly Ser Pro Ala
            260                 265                 270

Gly Ser Pro Thr Ser Thr Glu Glu Gly Thr Ser Glu Ser Ala Thr Pro
            275                 280                 285

Glu Ser Gly Pro Gly Thr Ser Thr Glu Pro Ser Glu Gly Ser Ala Pro
        290                 295                 300

Gly Thr Ser Thr Glu Pro Ser Glu Gly Ser Ala Pro Gly Ser Pro Ala
305                 310                 315                 320

Gly Ser Pro Thr Ser Thr Glu Glu Gly Thr Ser Thr Glu Pro Ser Glu
                325                 330                 335

Gly Ser Ala Pro Gly Thr Ser Thr Glu Pro Ser Glu Gly Ser Ala Pro
            340                 345                 350

Gly Thr Ser Glu Ser Ala Thr Pro Glu Ser Gly Pro Gly Thr Ser Thr
            355                 360                 365

Glu Pro Ser Glu Gly Ser Ala Pro Gly Thr Ser Glu Ser Ala Thr Pro
        370                 375                 380

Glu Ser Gly Pro Gly Ser Glu Pro Ala Thr Ser Gly Ser Glu Thr Pro
385                 390                 395                 400

Gly Thr Ser Thr Glu Pro Ser Glu Gly Ser Ala Pro Gly Thr Ser Thr
                405                 410                 415

Glu Pro Ser Glu Gly Ser Ala Pro Gly Thr Ser Glu Ser Ala Thr Pro
            420                 425                 430

Glu Ser Gly Pro Gly Thr Ser Glu Ser Ala Thr Pro Glu Ser Gly Pro
            435                 440                 445

Gly Ser Pro Ala Gly Ser Pro Thr Ser Thr Glu Glu Gly Thr Ser Glu
            450                 455                 460

Ser Ala Thr Pro Glu Ser Gly Pro Gly Ser Glu Pro Ala Thr Ser Gly
465                 470                 475                 480

Ser Glu Thr Pro Gly Thr Ser Glu Ser Ala Thr Pro Glu Ser Gly Pro
                485                 490                 495

Gly Thr Ser Thr Glu Pro Ser Glu Gly Ser Ala Pro Gly Thr Ser Thr
            500                 505                 510

Glu Pro Ser Glu Gly Ser Ala Pro Gly Thr Ser Thr Glu Pro Ser Glu
            515                 520                 525

Gly Ser Ala Pro Gly Thr Ser Thr Glu Pro Ser Glu Gly Ser Ala Pro
            530                 535                 540

Gly Thr Ser Thr Glu Pro Ser Glu Gly Ser Ala Pro Gly Thr Ser Thr
545                 550                 555                 560

Glu Pro Ser Glu Gly Ser Ala Pro Gly Ser Pro Ala Gly Ser Pro Thr

-continued

```
                565                 570                 575
Ser Thr Glu Glu Gly Thr Ser Thr Glu Pro Ser Glu Gly Ser Ala Pro
                580                 585                 590
Gly Thr Ser Glu Ser Ala Thr Pro Glu Ser Gly Pro Gly Ser Glu Pro
                595                 600                 605
Ala Thr Ser Gly Ser Glu Thr Pro Gly Thr Ser Glu Ser Ala Thr Pro
                610                 615                 620
Glu Ser Gly Pro Gly Ser Glu Pro Ala Thr Ser Gly Ser Glu Thr Pro
625                 630                 635                 640
Gly Thr Ser Glu Ser Ala Thr Pro Glu Ser Gly Pro Gly Thr Ser Thr
                645                 650                 655
Glu Pro Ser Glu Gly Ser Ala Pro Gly Thr Ser Glu Ser Ala Thr Pro
                660                 665                 670
Glu Ser Gly Pro Gly Ser Pro Ala Gly Ser Pro Thr Ser Thr Glu Glu
                675                 680                 685
Gly Ser Pro Ala Gly Ser Pro Thr Ser Thr Glu Glu Gly Ser Pro Ala
                690                 695                 700
Gly Ser Pro Thr Ser Thr Glu Glu Gly Thr Ser Glu Ser Ala Thr Pro
705                 710                 715                 720
Glu Ser Gly Pro Gly Thr Ser Thr Glu Pro Ser Glu Gly Ser Ala Pro
                725                 730                 735
Gly Thr Ser Glu Ser Ala Thr Pro Glu Ser Gly Pro Gly Ser Glu Pro
                740                 745                 750
Ala Thr Ser Gly Ser Glu Thr Pro Gly Thr Ser Glu Ser Ala Thr Pro
                755                 760                 765
Glu Ser Gly Pro Gly Ser Glu Pro Ala Thr Ser Gly Ser Glu Thr Pro
                770                 775                 780
Gly Thr Ser Glu Ser Ala Thr Pro Glu Ser Gly Pro Gly Thr Ser Thr
785                 790                 795                 800
Glu Pro Ser Glu Gly Ser Ala Pro Gly Ser Pro Ala Gly Ser Pro Thr
                805                 810                 815
Ser Thr Glu Glu Gly Thr Ser Glu Ser Ala Thr Pro Glu Ser Gly Pro
                820                 825                 830
Gly Ser Glu Pro Ala Thr Ser Gly Ser Glu Thr Pro Gly Thr Ser Glu
                835                 840                 845
Ser Ala Thr Pro Glu Ser Gly Pro Gly Ser Pro Ala Gly Ser Pro Thr
                850                 855                 860
Ser Thr Glu Glu Gly Ser Pro Ala Gly Ser Pro Thr Ser Thr Glu Glu
865                 870                 875                 880
Gly Thr Ser Thr Glu Pro Ser Glu Gly Ser Ala Pro Gly Thr Ser Glu
                885                 890                 895
Ser Ala Thr Pro Glu Ser Gly Pro Gly Thr Ser Glu Ser Ala Thr Pro
                900                 905                 910
Glu Ser Gly Pro Gly Thr Ser Glu Ser Ala Thr Pro Glu Ser Gly Pro
                915                 920                 925
Gly Ser Glu Pro Ala Thr Ser Gly Ser Glu Thr Pro Gly Ser Glu Pro
                930                 935                 940
Ala Thr Ser Gly Ser Glu Thr Pro Gly Ser Pro Ala Gly Ser Pro Thr
945                 950                 955                 960
Ser Thr Glu Glu Gly Thr Ser Thr Glu Pro Ser Glu Gly Ser Ala Pro
                965                 970                 975
Gly Thr Ser Thr Glu Pro Ser Glu Gly Ser Ala Pro Gly Ser Glu Pro
                980                 985                 990
```

```
Ala Thr Ser Gly Ser Glu Thr Pro  Gly Thr Ser Glu Ser  Ala Thr Pro
        995                 1000                1005

Glu Ser  Gly Pro Gly Thr Ser   Thr Glu Pro Ser Glu   Gly Ser Ala
    1010                1015                  1020

Pro Gly
    1025

<210> SEQ ID NO 2
<211> LENGTH: 168
<212> TYPE: PRT
<213> ORGANISM: Artificial Sequence
<220> FEATURE:
<223> OTHER INFORMATION: Ankyrin repeat protein

<400> SEQUENCE: 2

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Phe Asp Trp Met Gly Trp Thr Pro Leu His Leu Ala Ala His Glu Gly
        35                  40                  45

His Leu Glu Ile Val Glu Val Leu Leu Lys Asn Gly Ala Asp Val Asn
    50                  55                  60

Ala Thr Asp Val Ser Gly Tyr Thr Pro Leu His Leu Ala Ala Asp
65                  70                  75                  80

Gly His Leu Glu Ile Val Glu Val Leu Leu Lys His Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Gly
145                 150                 155                 160

Gly Gly Ser Gly Gly Gly Ser Cys
                165

<210> SEQ ID NO 3
<211> LENGTH: 135
<212> TYPE: PRT
<213> ORGANISM: Artificial Sequence
<220> FEATURE:
<223> OTHER INFORMATION: Ankyrin repeat protein

<400> SEQUENCE: 3

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Arg Asp Ser Thr Gly Trp Thr Pro Leu His Leu Ala Ala Pro Trp Gly
        35                  40                  45

His Pro Glu Ile Val Glu Val Leu Leu Lys Asn Gly Ala Asp Val Asn
    50                  55                  60

Ala Ala Asp Phe Gln Gly Trp Thr Pro Leu His Leu Ala Ala Ala Val
65                  70                  75                  80

Gly His Leu Glu Ile Val Glu Val Leu Leu Lys Tyr Gly Ala Asp Val
```

```
                85                  90                  95
Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala Gly Gly
            115                 120                 125

Gly Ser Gly Gly Gly Ser Cys
        130                 135

<210> SEQ ID NO 4
<211> LENGTH: 540
<212> TYPE: PRT
<213> ORGANISM: Artificial Sequence
<220> FEATURE:
<223> OTHER INFORMATION: Ankyrin repeat protein

<400> SEQUENCE: 4

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
            20                  25                  30

Ala Asp Ser Thr Gly Trp Thr Pro Leu His Leu Ala Val Pro Trp Gly
        35                  40                  45

His Leu Glu Ile Val Glu Val Leu Leu Lys Tyr Gly Ala Asp Val Asn
    50                  55                  60

Ala Lys Asp Phe Gln Gly Trp Thr Pro Leu His Leu Ala Ala Ala Ile
65                  70                  75                  80

Gly His Gln Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala Gly Ser
            115                 120                 125

Gly Ser Ala Ser Pro Ala Ala Pro Ala Pro Ala Ser Pro Ala Ala Pro
        130                 135                 140

Ala Pro Ser Ala Pro Ala Ala Ser Pro Ala Ala Pro Ala Pro Ala Ser
145                 150                 155                 160

Pro Ala Ala Pro Ala Pro Ser Ala Pro Ala Ala Ser Pro Ala Ala Pro
            165                 170                 175

Ala Pro Ala Ser Pro Ala Ala Pro Ala Pro Ser Ala Pro Ala Ala Ser
            180                 185                 190

Pro Ala Ala Pro Ala Pro Ala Ser Pro Ala Ala Pro Ala Pro Ser Ala
            195                 200                 205

Pro Ala Ala Ser Pro Ala Ala Pro Ala Pro Ala Ser Pro Ala Ala Pro
        210                 215                 220

Ala Pro Ser Ala Pro Ala Ala Ser Pro Ala Ala Pro Ala Pro Ala Ser
225                 230                 235                 240

Pro Ala Ala Pro Ala Pro Ser Ala Pro Ala Ala Ser Pro Ala Ala Pro
            245                 250                 255

Ala Pro Ala Ser Pro Ala Ala Pro Ala Pro Ser Ala Pro Ala Ala Ser
            260                 265                 270

Pro Ala Ala Pro Ala Pro Ala Ser Pro Ala Ala Pro Ala Pro Ser Ala
            275                 280                 285

Pro Ala Ala Ser Pro Ala Ala Pro Ala Pro Ala Ser Pro Ala Ala Pro
        290                 295                 300

Ala Pro Ser Ala Pro Ala Ala Ser Pro Ala Ala Pro Ala Pro Ala Ser
```

```
                    305                 310                 315                 320
Pro Ala Ala Pro Ala Pro Ser Ala Pro Ala Ser Pro Ala Ala Pro
                325                 330                 335
Ala Pro Ala Ser Pro Ala Ala Pro Ala Pro Ser Ala Pro Ala Ser
                340                 345                 350
Pro Ala Ala Pro Ala Pro Ser Ala Ala Pro Ala Pro Ser Ala
            355                 360                 365
Pro Ala Ala Ser Pro Ala Ala Pro Ala Pro Ala Ser Pro Ala Ala Pro
        370                 375                 380
Ala Pro Ser Ala Pro Ala Ala Ser Pro Ala Ala Pro Ala Pro Ala Ser
385                 390                 395                 400
Pro Ala Ala Pro Ala Pro Ser Ala Pro Ala Ala Ser Pro Ala Ala Pro
                405                 410                 415
Ala Pro Ala Ser Pro Ala Ala Pro Ala Pro Ser Ala Pro Ala Ala Ser
                420                 425                 430
Pro Ala Ala Pro Ala Pro Ala Ser Pro Ala Ala Pro Ala Pro Ser Ala
            435                 440                 445
Pro Ala Ala Ser Pro Ala Ala Pro Ala Pro Ser Pro Ala Ala Pro
        450                 455                 460
Ala Pro Ser Ala Pro Ala Ala Ser Pro Ala Ala Pro Ala Pro Ala Ser
465                 470                 475                 480
Pro Ala Ala Pro Ala Pro Ser Ala Pro Ala Ala Ser Pro Ala Ala Pro
                485                 490                 495
Ala Pro Ala Ser Pro Ala Ala Pro Ala Pro Ser Ala Pro Ala Ala Ser
                500                 505                 510
Pro Ala Ala Pro Ala Pro Ala Ser Pro Ala Ala Pro Ala Pro Ser Ala
            515                 520                 525
Pro Ala Ala Ser Pro Ala Ala Pro Ala Pro Ala Ser
        530                 535                 540

<210> SEQ ID NO 5
<211> LENGTH: 135
<212> TYPE: PRT
<213> ORGANISM: Artificial Sequence
<220> FEATURE:
<223> OTHER INFORMATION: Ankyrin repeat protein 5

<400> SEQUENCE: 5

Gly Ser Asp Leu Gly Lys Lys Leu Leu Glu Ala Ala Arg Val Gly Gln
1               5                   10                  15

Asp Asp Glu Val Arg Ile Leu Met Ala Asp Gly Ala Asp Val Asn Ala
                20                  25                  30

Ser Asp Phe Lys Gly Asp Thr Pro Leu His Leu Ala Ala Ser Gln Gly
            35                  40                  45

His Leu Glu Ile Val Glu Val Leu Leu Lys Tyr Gly Ala Asp Val Asn
        50                  55                  60

Ala Tyr Asp Met Leu Gly Trp Thr Pro Leu His Leu Ala Ala Asp Leu
65                  70                  75                  80

Gly His Leu Glu Ile Val Glu Val Leu Leu Lys Tyr Gly Ala Asp Val
                85                  90                  95

Asn Ala Gln Asp Arg Phe Gly Lys Thr Ala Phe Asp Ile Ser Ile Asp
            100                 105                 110

Asn Gly Asn Glu Asp Leu Ala Glu Ile Leu Gln Lys Ala Ala Gly Ser
        115                 120                 125

Pro Ser Thr Ala Asp Gly Cys
    130                 135
```

```
                130                 135

<210> SEQ ID NO 6
<211> LENGTH: 130
<212> TYPE: PRT
<213> ORGANISM: Artificial Sequence
<220> FEATURE:
<223> OTHER INFORMATION: Ankyrin repeat protein

<400> SEQUENCE: 6

Gly Ser Asp Leu Gly Lys Lys Leu Leu Glu Ala Val Arg Ala Gly Gln
1               5                   10                  15

Asp Asp Glu Val Arg Ile Leu Met Thr Asn Gly Ala Asp Val Asn Ala
            20                  25                  30

Lys Asp Gln Phe Gly Phe Thr Pro Leu Gln Leu Ala Ala Tyr Asn Gly
        35                  40                  45

His Leu Glu Ile Val Glu Val Leu Leu Lys Tyr Gly Ala Asp Val Asn
    50                  55                  60

Ala Phe Asp Ile Phe Gly Trp Thr Pro Leu His Leu Ala Ala Asp Leu
65                  70                  75                  80

Gly His Leu Glu Ile Val Glu Val Leu Leu Lys Asn Gly Ala Asp Val
                85                  90                  95

Asn Ala Gln Asp Lys Phe Gly Arg Thr Ala Phe Asp Ile Ser Ile Asp
            100                 105                 110

Asn Gly Asn Glu Asp Leu Ala Glu Ile Leu Gln Lys Ala Ala Ser Gly
        115                 120                 125

Ser Cys
    130

<210> SEQ ID NO 7
<211> LENGTH: 168
<212> TYPE: PRT
<213> ORGANISM: Artificial Sequence
<220> FEATURE:
<223> OTHER INFORMATION: Ankyrin repeat protein

<400> SEQUENCE: 7

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Val Asp Tyr Ile Gly Trp Thr Pro Leu His Leu Ala Ala Tyr Gly
        35                  40                  45

His Leu Glu Ile Val Glu Val Leu Leu Lys Tyr Ser Ala Asp Val Asn
    50                  55                  60

Ala Glu Asp Phe Ala Gly Tyr Thr Pro Leu His Leu Ala Ala Ser Asn
65                  70                  75                  80

Gly His Leu Glu Ile Val Glu Val Leu Leu Lys Tyr Gly Ala Asp Val
                85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Tyr Gly Ala Asp
        115                 120                 125

Val Asn Thr Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Gly
145                 150                 155                 160
```

```
Ser Pro Ser Thr Ala Asp Gly Cys
            165

<210> SEQ ID NO 8
<211> LENGTH: 9
<212> TYPE: PRT
<213> ORGANISM: Artificial Sequence
<220> FEATURE:
<223> OTHER INFORMATION: Polypeptide linker

<400> SEQUENCE: 8

Gly Gly Gly Ser Gly Gly Gly Ser Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Polypeptide linker

<400> SEQUENCE: 9

Gly Ser Pro Ser Thr Ala Asp Gly Cys
1               5
```

METHOD OF TREATING AMD IN PATIENTS REFRACTORY TO ANTI-VEGF THERAPY

CROSS-REFERENCE TO RELATED APPLICATIONS

This application claims the benefit of U.S. Provisional Application No. 61/643,878 filed on May 7, 2012, U.S. Provisional Application No. 61/728,017 filed on Nov. 19, 2012, and U.S. Provisional Application No. 61/731,238 filed on Nov. 29, 2012. The entire contents of all three applications are incorporated herein by reference.

BACKGROUND

The retina is a thin layer of neural tissue lining the inner surface of the back of the eye. The retina consists of various kinds of neurons, the most familiar of which are the photoreceptors responsible for vision: rods, which are more sensitive to light, and cones, which are more sensitive to color. The cones are highly concentrated in the macula, the small, central portion of the retina. It is this portion of the eye that is responsible for central, high acuity vision.

Diseases of the retina, and the macula in particular, are the leading cause of vision impairment and blindness in those over 50 years of age in developed countries. These diseases include age-related macular degeneration, myopic macular degeneration, diabetic macular edema, diabetic retinopathy, branch retinal vein occlusion, and central retinal vein occlusion. Macular degeneration can occur in children, as well.

Some of these diseases can be treated with agents that inhibit a protein called vascular endothelial growth factor A (VEGF-A). VEGF-A stimulates the growth of blood vessels. In the exudative (or vascular) form of age-related macular degeneration, abnormally high levels of VEGF stimulate the growth of new blood vessels into the macula causing irreversible damage to photoreceptors; in addition, these newly formed blood vessels leak blood and proteins into the retina, causing a scar to form in the area that was previously occupied by photoreceptors. Inhibiting VEGF-A blocks the formation of these new vessels, and blocks the leakage of blood and proteins, thus preserving vision.

There are a few drugs that are used to inhibit VEGF-A in the eye. These include ranibizumab, bevacizumab, aflibercept, and, to a lesser extent, pegaptanib. They are effective to various degrees, but all suffer from two significant shortcomings: they are not effective in all patients, and they must be dosed frequently (at least every four to eight weeks) by a method of administration which many patients find disagreeable.

Ranibizumab is a antibody fragment derived from the same parent mouse antibody as bevacizumab. It is sold under the brand name LUCENTIS® in the United States. Ranibizumab is indicated for the treatment of neovascular (exudative) age-related macular degeneration, macular edema following retinal vein occlusion, and diabetic macular edema.

Ranibizumab is administered at a dose of 0.3 mg or 0.5 mg, depending on the condition treated, every 28 days. The drug is injected by means of syringe directly into the vitreous humor of the eye, the clear gelatinous material that comprises most of the volume of the eye. An example is shown in FIG. 1. An intravitreal injection can be injected through the pars plana, 3 mm to 4 mm posterior to the limbus. For age-related macular degeneration, 0.5 mg ranibizumab is administered to the affected eye by intravitreal injection approximately every 28 days. The prescribing literature that accompanies the product states that "treatment may be reduced to one injection every 3 months after the first four injections if monthly injections are not feasible," but that such doses are "less effective," and that "dosing every 3 months will lead to an approximate 5-letter (1-line) loss of visual acuity benefit, on average, over the following 9 months" compared to continued monthly dosing.

Bevacizumab is a humanized monoclonal antibody inhibitor of VEGF-A. It is sold under the brand name AVASTIN® in the United States. Bevacizumab is indicated as a single-use therapy for glioblastoma and as an adjunctive therapy for metastatic colorectal cancer, non-squamous non-small cell lung cancer, and metastatic renal cell carcinoma. It is also used, off-label, for the treatment of those conditions for which ranibizumab is indicated. The dosing schedule is the same as for ranibizumab.

Aflibercept is a recombinant fusion protein comprising extracellular domains of human VEGF receptors 1 and 2 fused to the Fc portion of human IgG1. It is sold under the brand name EYLEA® in the United States. Aflibercept is indicated for the treatment of neovascular (exudative) age-related macular degeneration, administered in a 2 mg dose by intravitreal injection every 4 weeks for the first 12 weeks, followed by 2 mg via intravitreal injection once every 8 weeks. The drug may also be dosed as frequently as 2 mg every 4 weeks.

Pegaptanib is a single strand of nucleic acid, more specifically, an oligonucleotide of twenty-eight nucleotides, that binds to VEGF-A165. It is sold under the brand name MACUGEN® in the United States. Pegaptanib is approved for the treatment of treatment of neovascular (exudative) age-related macular degeneration, administered in a 0.3 mg dose every 6 weeks by intravitreous injection. The drug is not as effective as ranibizumab, bevacizumab, or aflibercept and so is not as frequently used.

Despite the effectiveness of ranibizumab, bevacizumab, aflibercept, and pegaptanib, there are still patients who do not respond to those drugs. Moreover, those drugs require frequent administration every four to eight weeks. That may not seem so bad—and indeed it would not be so, were those drugs swallowed as a pill, or applied topically as an eye drop. Instead, those drugs are administered by a needle that pierces the front of the eye (including, but not limited to the conjunctiva and sclera) and extends into the vitreous of the eye where the drug is delivered. The procedure is safe, when performed by trained personnel, but readers who doubt that anyone should object to undergoing such a procedure every four weeks are invited to take a needle, hold it within proximity to the eye, and contemplate the path required to reach the vitreous. There is therefore a need in the art for therapies capable of treating patients who desire a relief from diseases of the retina whom ranibizumab, bevacizumab, aflibercept, or pegaptanib do not aid, for patients who desire less frequent treatment, and for patients desire both.

SUMMARY OF THE INVENTION

The inventors have surprisingly discovered that the anti-VEGF compositions and methods of the invention may be used to treat exudative age-related macular degeneration and other conditions of the eye with surprisingly fewer injections than ranibizumab, bevacizumab, aflibercept, and pegaptanib require. Like those drugs, the compositions of the inventions also inhibit VEGF-A, and so have the same mechanism of action (that is, they work in much the same way)—yet the compositions and methods of the invention may be used to treat patients who ranibizumab, bevacizumab, aflibercept, and pegaptanib cannot treat. One can also administer the drugs to treat ocular conditions such as age-related macular degeneration, diabetic macular edema, pathological myopia branch retinal vein occlusion, or central retinal vein occlusion.

Accordingly, in an embodiment, a method of inhibiting binding between VEGF-Axxx and VEGFR-2 includes the step of administering to a patient in need of such inhibition, at a frequency between 8 weeks and 16 weeks, a dose of about 1 mg to about 4 mg of a recombinant binding protein comprising an ankyrin repeat domain, wherein the ankyrin domain binds VEGF-Axxx with a Kd below $10^9$M. In some embodiments, the binding protein further includes a polyethylene glycol moiety of at least 5 kDa molecular weight. According to some embodiments, the N-terminal capping module of the ankyrin repeat domain comprises an Asp residue at position 5. In some embodiments, the ankyrin repeat domain competes for binding to VEGF-Axxx with the ankyrin repeat domains of SEQ ID NO:1 or 3. In some embodiments, the ankyrin repeat domain is selected from the group consisting of the ankyrin repeat domains of SEQ ID NOS: 1 to 7. According to some embodiments, the binding protein inhibits VEGF-Axxx binding to VEGFR-1. In some embodiments, the ankyrin repeat domain is conjugated at its C-terminus via a peptide bond to a polypeptide linker and a C-terminal Cys residue, wherein the thiol of the C-terminal Cys is further conjugated to a maleimide-coupled polyethylene glycol. In some embodiments, the maleimide-coupled polyethylene glycol is α-[3-(3-maleimido-1-oxo-propyl)amino]propyl-ω-methoxy-polyoxyethylene. According to some embodiments, the binding protein is an ankyrin repeat protein selected from the group consisting of the ankyrin repeat proteins of SEQ ID NOS: 2, 3, 5, 6 or 7. In some embodiments, the polyethylene glycol moiety has a molecular weight of about 20 kDa. In some embodiments, the binding protein includes the ankyrin repeat protein of SEQ ID NO:3 and the thiol of the C-terminal Cys of the ankyrin repeat protein is further conjugated to a maleimide-coupled polyethylene glycol. According to some embodiments, the maleimide-coupled polyethylene glycol is α-[3-(3-maleimido-1-oxopropyl)amino]propyl-ω-methoxy-polyoxyethylene, and the polyethylene glycol moiety has a molecular weight of at least 10 kDa. According to some embodiments, the binding protein is administered with a pharmaceutically acceptable carrier and/or diluents, in some embodiments, the carrier is PBS. In some embodiments, the binding protein is administered by intravitreal injection. According to some embodiments, the binding protein is administered every 8, 9, 10, 11, 12, 13, 14, 15, or 16 weeks. In some embodiments, the binding protein is administered at a dose of 2 mg, 3 mg, or 4 mg, or at a dose of about 2.0 mg, about 3.0 mg, or about 4.0 mg. According to some embodiments, the method is used to treat age-related macular degeneration, diabetic macular edema, pathological myopia branch retinal vein occlusion, or central retinal vein occlusion in a patient having that condition. According to some embodiments, the patient is refractory to ranibizumab, bevacizumab, aflibercept, or pegaptanib therapy. In some embodiments, the patient refractory to ranibizumab, bevacizumab, aflibercept, or pegaptanib therapy has less than a 20% decrease in the center 1 mm$^2$ area of the macula after 3 intravitreal injections of ranibizumab, bevacizumab, or aflibercept. In some embodiments, the patient is refractory to one dose of ranizumab therapy. In some embodiments, the patient is refractory to one dose of bevacizumab therapy. In some embodiments, the patient is refractory to one dose of aflibercept therapy. In some embodiments, the patient is refractory to one dose of pegaptanib therapy.

These and other embodiments are described in greater detail below.

BRIEF DESCRIPTION OF THE FIGURES

These and other features will now be described with reference to the drawings summarized below. These drawings and the associated description are provided to illustrate one or more embodiments and not to limit the scope of the invention.

FIG. 3a shows central retina thickness in human patients, refractory to LUCENTIS® and/or AVASTIN® therapy, after receiving via injection into the vitreous 3.0 mg of a composition according to the invention comprising the ankyrin repeat domains of SEQ ID NO: 3. The composition was dissolved in PBS and administered via intravitreal injection in a 50 µl volume.

FIG. 3b shows central retina thickness in human patients, refractory to LUCENTIS® and/or AVASTIN® therapy, after receiving via injection into the vitreous 4.2 mg of a composition according to the invention comprising the ankyrin repeat domains of SEQ ID NO: 3. The composition was dissolved in PBS and administered via intravitreal injection in a 50 µl volume.

DETAILED DESCRIPTION OF THE INVENTION

Vascular Endothelial Growth Factor

Figure 1:
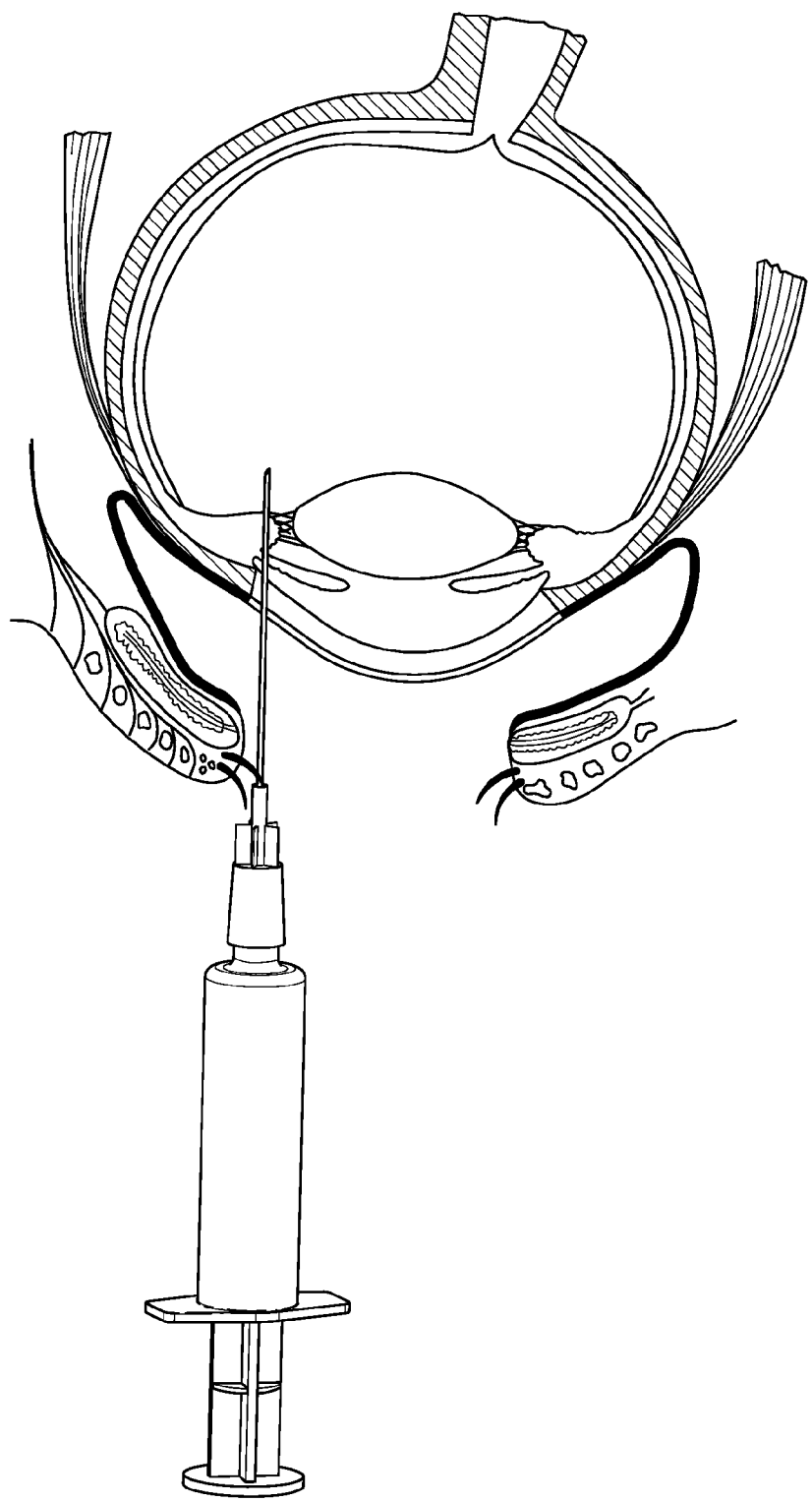
FIG. 1 illustrates an example injection of a drug by means of syringe directly into the vitreous humor of the eye.

Angiogenesis, the growth of new blood vessels from pre-existing vasculature and increased vessel exudation are key processes in several pathological conditions, including tumor growth and eye diseases, in particular ocular neovascularization and retinal ischemic diseases such as age-related macular degeneration or diabetic macular edema (Carmeliet, P., Nature 438, 932-936, 2005). Vascular endothelial growth factors stimulate angiogenesis and lymphangiogenesis by activating VEGF receptor (VEGFR) tyrosine kinases in endothelial cells (Ferrara, N., Gerber, H. P. and LeCouter, J., Nature Med. 9, 669-676, 2003).

The mammalian VEGF family consists of five glycoproteins referred to as VEGF-A, VEGF-B, VEGF-C, VEGF-D (also known as FIGF) and placenta growth factor (PlGF, also known as PGF). VEGF-A has been shown to be an effective target for anti-angiogenic therapy (Ellis, L. M. and Hicklin, D. J., Nature Rev. Cancer 8, 579-591, 2008). The VEGF-A ligands bind to and activate three structurally similar type III receptor tyrosine kinases, designated VEGFR-1 (also known as FLT1), VEGFR-2 (also known as KDR) and VEGFR-3 (also known as FLT4). The VEGF ligands have distinctive binding specificities for each of these tyrosine kinase receptors, which contribute to their diversity of function. In response to ligand binding, the VEGFR tyrosine kinases activate a network of distinct downstream signaling pathways. VEGFR-1 and VEGFR-2 are primarily found on the vascular endothelium whereas VEGFR-3 is mostly found on the lymphatic endothelium. These receptors all have an extracellular domain, a single transmembrane region and a consensus tyrosine kinase sequence interrupted by a kinase-insert domain. More recently neuropilin (NRP-1), originally identified as a receptor for the semaphorin/collapsin family of neuronal guidance mediators, was shown to act as an isoform specific receptor for VEGF-A. Various isoforms of VEGF-A are known that are generated by alternative splicing from eight exons within the VEGF-A gene. All isoforms contain exons 1-5 and the terminal exon, exon 8. Exons 6 and 7, which encode heparin-binding domains, can be included or excluded. This gives rise to a family of proteins termed according to their amino acid number: VEGF-A165, VEGF-A121, VEGF-A189, and so on. Exon 8, however, contains two 3' splice sites in the nucleotide sequences, which can be used by the cell to generate two families of isoforms with identical length, but differing C-terminal amino acid sequences (Varey, A. H. R. et al., British J. Cancer 98, 1366-1379, 2008). VEGF-Axxx ("xxx" denotes the amino acid number of the mature protein), the pro-angiogenic family of isoforms, is generated by use of the most proximal sequence in exon 8 (resulting in the inclusion of exon 8a). The more recently described anti-angiogenic VEGF-Axxxb isoforms are generated by the use of a distal splice site, 66 bp further along the gene from the proximal splice site. This results in splicing out of exon 8a and the production of mRNA sequences that encode the VEGF-Axxxb family. VEGF-A165 is the predominant pro-angiogenic isoform and is commonly overexpressed in a variety of human solid tumors. VEGF-A165b was the first of the exon 8b-encoded isoforms identified and was shown to have anti-angiogenic effects (Varey et al., loc. cit; Konopatskaya, O. et al., Molecular Vision 12, 626-632, 2006). It is an endogenous inhibitory form of VEGF-A, which decreases VEGF-A induced proliferation and migration of endothelial cells. Although it can bind to VEGFR-2, VEGF-A165b binding does not result in receptor phosphorylation or activation of the downstream signaling pathways.

Recombinant Binding Proteins

The method of the invention administers a binding protein comprising a binding domain comprising a designed ankyrin repeat domain. Examples of such designed ankyrin repeat domains are described in U.S. Pat. Nos. 7,417,130 and 8,110,653, the entire contents of both of which are incorporated herein by reference. Those patents further contain a general description of repeat protein features, techniques and applications.

The term "repeat proteins" refers to a protein comprising one or more repeat domains. In one embodiment, each of the repeat proteins comprises up to four repeat domains. In another embodiment, each of the repeat proteins comprises up to two repeat domains. In another embodiment, each of the repeat proteins comprises only one repeat domain. The repeat protein may also comprise additional non-repeat protein domains, polypeptide tags and/or polypeptide linkers.

The term "repeat domain" refers to a protein domain comprising two or more consecutive repeat units (modules) as structural units, wherein the structural units have the same fold, and stack tightly to create, for example, a superhelical structure having a joint hydrophobic core.

The term "designed repeat protein" and "designed repeat domain" refer to a repeat protein or repeat domain, respectively, obtained as the result of the inventive procedure explained in U.S. Pat. Nos. 7,417,130 and 8,110,653. Designed repeat proteins and designed repeat domains are synthetic and not from nature. They are man-made proteins or domains, respectively, obtained by expression of correspondingly designed nucleic acids.

Mammalian VEGF-A exists as two families of alternative spliced isoforms: (i) the pro-angiogenic "VEGF-Axxx" isoforms generated by proximal splicing of exon 8 and (ii) the anti-angiogenic "VEGF-Axxxb" isoforms generated by distal splicing of exon 8. In one embodiment, the binding domain according to the invention is specific for the pro-angiogenic VEGF-Axxx of dog, rabbit, monkey or human origin. In another embodiment, the binding domain according to the invention is specific for the pro-angiogenic VEGF-Axxx of human origin. In another embodiment, the binding domain according to the invention is specific for human VEGF-A165.

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire a defined three-dimensional arrangement by forming secondary or tertiary structures, is termed "protein domain." Such protein domains are well known to the practitioner skilled in the art.

The term "recombinant" as used in recombinant protein, recombinant protein domain and the like, means that the polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen). When such a constructed recombinant expression plasmid is inserted into a bacteria (e.g. E. coli), this bacteria can produce the polypeptide encoded by this recombinant DNA. The correspondingly produced polypeptide is called a recombinant polypeptide.

The term "polypeptide tag" refers to an amino acid sequence attached to a polypeptide/protein, wherein the amino acid sequence is useful for the purification, detection, or targeting of the polypeptide/protein, or wherein the amino acid sequence improves the physicochemical behavior of the polypeptide/protein, or wherein the amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His, myc, FLAG, or Strep-tags or moieties such as enzymes (for example enzymes like alkaline phosphatase), which allow the detection of the polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in U.S. Pat. Nos. 7,417,130 and 8,110,653. Examples of such linkers are glycine-serine-linkers and proline-threonine-linkers of variable lengths. In one embodiment, the linkers have a length of between 2 and 24 amino acids; in another embodiment, the linkers have a length of between 2 and 16 amino acids.

The term "polypeptide" relates to a molecule consisting of one or more chains of multiple, i.e. two or more, amino acids linked via peptide bonds. In one embodiment, a polypeptide consists of more than eight amino acids linked via peptide bonds.

The term "polymer moiety" refers to either a proteinaceous polymer moiety or a non-proteinaceous polymer moiety. In one embodiment, a "proteinaceous polymer moiety" is a polypeptide that does not form a stable tertiary structure while not forming more than 10% (or, not more than 5%, not more than 2%, not more than 1%, and not more than any detectable amount, as determined by size exclusion chromatography (SEC)) of oligomers or aggregates when stored at a concentration of about 0.1 mM in PBS at RT for one month. Such proteinaceous polymer moieties run at an apparent molecular weight in SEC that is higher than their effective molecular weight when using globular proteins as molecular weight standards for the SEC. In one embodiment, the apparent molecular weight of the proteinaceous polymer moieties determined by SEC is 1.5×, 2× or 2.5× higher than their effective molecular weight calculated from their amino acid sequence. In one embodiment, the apparent molecular weights of the non-proteinaceous polymer moieties determined by SEC is 2×, 4× or 8× higher than their effective molecular weight calculated from their molecular composition. In one embodiment, more than 50%, 70% or even 90% of the amino acids of the proteinaceous polymer moiety do not form stable secondary structures at a concentration of about 0.1 mM in PBS at RT as determined by Circular Dichroism (CD) measurements. In one embodiment, the proteinaceous polymer shows a typical near UV CD-spectra of a random coil conformation. Such CD analyses are well known to the person skilled in the art. One can also use proteinaceous polymer moieties that comprise more than 50, 100, 200, 300, 400, 500, 600, 700 or 800 amino acids.

Examples of proteinaceous polymer moieties are XTEN® (a registered trademark of Amunix; WO 07/103515) polypeptides, or polypeptides comprising proline, alanine and serine residues as described in WO 08/155134. Such proteinaceous polymer moieties can be covalently attached to, for example, a binding domain of the invention by the generation of genetic fusion polypeptides using standard DNA cloning technologies, followed by their standard expression and purification. Examples of binding proteins comprising a repeat domain binding VEGF-Axxx and such a proteinaceous polymer moiety are shown in SEQ ID NO:1 and SEQ ID NO:4. The amino acid positions from 1 to 159 of SEQ ID NO:1 correspond to the repeat domain and the amino acid position 161 to 1 025 of SEQ ID NO:1 correspond to the proteinaceous polymer moiety. The amino acid positions from 1 to 126 of SEQ ID NO:4 correspond to the repeat domain and the amino acid positions 131 to 640 of SEQ ID NO:4 correspond to the proteinaceous polymer moiety.

A polymer moiety of the invention may vary widely in molecular weight (i.e. from about 1 kDa to about 150 kDa). In one embodiment, the polymer moiety has a molecular weight of at least 2 kDa, 5 kDa, 10 kDa, 20 kDa, 30 kDa, 50 kDa, 70 kDa or 100 kDa.

In one embodiment, the polymer moiety is connected by a polypeptide linker to a binding domain. Examples of such polypeptide linkers are the amino acids 1 to 8 of SEQ ID NO:8 and SEQ ID NO:9.

Examples of non-proteinaceous polymer moieties are hydroxyethyl starch (HES), polyethylene glycol (PEG), polypropylene glycol, or polyoxyalkylene. The term "PEGylated" means that a PEG moiety is covalently attached to, for example, a polypeptide of the invention. Examples of repeat proteins containing a polypeptide linker between the repeat domain and a C-terminal Cys residue useful for binding a non-proteinaceous polymer moiety are SEQ ID NO:2, 3, 5, 6 and 7. In some embodiments, PEG, if used, can be either in a linear or branched arrangement.

In a specific embodiment, a PEG moiety or any other non-proteinaceous polymer can, e.g., be coupled to a cysteine thiol via a maleimide linker with the cysteine being coupled via a peptide linker to the N- or C-terminus of a binding domain as described herein (e.g. SEQ ID NO:3).

The term "binding protein" refers to a protein comprising one or more binding domains and, in one embodiment, one or more polymer moieties as further explained below. In one embodiment, the binding protein comprises up to four binding domains. In one embodiment, the binding protein comprises up to two binding domains. In another embodiment, the binding protein has only one binding domain. Furthermore, any such binding protein may comprise additional protein domains that are not binding domains, multimerization moieties, polypeptide tags, polypeptide linkers and/or a single Cys residue. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. The single Cys residue may be used for conjugating other moieties to the polypeptide, for example, by using the maleimide chemistry well known to the person skilled in the art.

In one embodiment, the binding protein comprises up to four polymer moieties. In another embodiment, the binding protein comprises up to two polymer moieties. In another embodiment, the binding protein only has one polymer moiety.

In one embodiment, the binding protein has an apparent molecular weight of about 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 200 kDa, 300 kDa, 400 kDa, 500 kDa, 600 kDa, 700 kDa, 800 kDa, 900 kDa, or 1,000 kDa when analyzed at a concentration of 0.1 mM in PBS at RT by SEC using globular proteins as molecular weight standards. In one embodiment, the binding protein has an apparent molecular weight of 34 kDa.

Those skilled in the art will appreciate the meaning of various terms of degree used herein. For example, as used herein in the context of referring to an amount (e.g., "about 10 kDa"), the term "about" represents an amount close to and including the stated amount that still performs a desired function or achieves a desired result, e.g. "about 10 kDa"

can include 10 kDa and amounts close to 10 kDa that still perform a desired function or achieve a desired result. For example, the term "about" can refer to an amount that is within 10% or less of, within 5% or less of, within 0.1% or less of, or within 0.01% or less of the stated amount.

The term "binding domain" means a protein domain exhibiting the same "fold" (three-dimensional arrangement) as a protein scaffold and having a predetermined property, as defined below. Such a binding domain may be obtained by rational, or most commonly, combinatorial protein engineering techniques, skills which are known in the art (Skerra, 2000, loc. cit; Binz et al., 2005, loc. cit). For example, a binding domain having a predetermined property can be obtained by a method comprising the steps of (a) providing a diverse collection of protein domains exhibiting the same fold as a protein scaffold as defined further below; and (b) screening the diverse collection and/or selecting from the diverse collection to obtain at least one protein domain having the predetermined property. The diverse collection of protein domains may be provided by several methods in accordance with the screening and/or selection system being used, and may comprise the use of methods well known to the person skilled in the art, such as phage display or ribosome display.

The term "protein scaffold" means a protein with exposed surface areas in which amino acid insertions, substitutions or deletions are highly tolerable. Examples of protein scaffolds that can be used to generate binding domains of the present invention are antibodies or fragments thereof such as single-chain Fv or Fab fragments, protein A from *Staphylococcus aureus*, the bilin binding protein from *Pieris brassicae* or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, the predetermined property is binding to a target.

In one embodiment, the binding domain of the invention does not comprise an immunoglobulin fold as present in antibodies and/or the fibronectin type III domain. An immunoglobulin fold is a common all-β protein fold that consists of a 2-layer sandwich of about 7 anti-parallel β-strands arranged in two β-sheets. Immunoglobulin folds are well known to the person skilled in the art. For example, such binding domains comprising an immunoglobulin fold are described in WO 07/080392 or WO 08/097497.

In another embodiment, the binding domain of the invention does not comprise an immunoglobulin-like domain as found in VEGFR-1 or VEGFR-2. Such binding domains are described in WO 00/075319.

In one embodiment, the binding domain comprises between 70 amino acids and 300 amino acids; in another embodiment, the binding comprises between 100 amino acids and 200 amino acids.

In one embodiment, the binding domain is devoid of a free Cys residue. A free Cys residue is not involved in the formation of a disulfide bond. In another embodiment, the binding domain is free of any Cys residue.

In one embodiment, the binding proteins of the invention may be expressed in eukaryotic or prokaryotic cells, such as bacterial cells, or by using a cell-free in vitro expression system.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein the "repeat units" are found in multiple copies, and which exhibit a defined folding topology common to all the motifs determining the fold of the protein. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins." The amino acid sequences of the individual repeat units of a repeat protein may have a significant number of mutations, substitutions, additions and/or deletions when compared to each other, while still substantially retaining the general pattern, or motif, of the repeat units.

The term "repeat sequence motif" refers to an amino acid sequence, which is deduced from one or more repeat units. In one embodiment, the repeat units are from repeat domains having binding specificity for the same target.

The term "folding topology" refers to the tertiary structure of the repeat units. The folding topology will be determined by stretches of amino acids forming at least parts of α-helices or β-sheets, or amino acid stretches forming linear polypeptides or loops, or any combination of α-helices, β-sheets and/or linear polypeptides/loops.

The term "consecutive" refers to an arrangement wherein the repeat units or repeat modules are arranged in tandem. In designed repeat proteins, there are at least 2 repeat units, but usually about 2 repeat units to 6 repeat units, but there may also be 6 or more repeat units or 20 or more repeat units. In most cases, repeat units will exhibit a high degree of sequence identity (same amino acid residues at corresponding positions) or sequence similarity (amino acid residues being different, but having similar physicochemical properties), and some of the amino acid residues might be key residues being strongly conserved in the different repeat units found in naturally occurring proteins. However, a high degree of sequence variability by amino acid insertions and/or deletions, and/or substitutions between the different repeat units found in naturally occurring proteins will be possible as long as the common folding topology is maintained.

Methods for directly determining the folding topology of repeat proteins by physico-chemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins.

"Repeat modules" may comprise positions with amino acid residues present in all copies of corresponding repeat modules ("fixed positions") and positions with differing or "randomized" amino acid residues ("randomized positions").

The term "capping module" refers to a polypeptide fused to the N- or C-terminal repeat module of a repeat domain, wherein the capping module forms tight tertiary interactions with the repeat module thereby providing a cap that shields the hydrophobic core of the repeat module at the side not in contact with the consecutive repeat module from the solvent. The N- and/or C-terminal capping module may be, or may be derived from, a capping unit or other domain found in a naturally occurring repeat protein adjacent to a repeat unit. The term "capping unit" refers to a naturally occurring folded polypeptide, wherein the polypeptide defines a particular structural unit which is N- or C-terminally fused to a repeat unit, wherein the polypeptide forms tight tertiary interactions with the repeat unit thereby providing a cap that shields the hydrophobic core of the repeat unit at one side from the solvent. Such capping units may have sequence similarities to the repeat sequence motif. Capping modules and capping repeats are described in U.S. Pat. Nos. 7,417,130 and 8,110,653. For example, the N-terminal capping module of SEQ ID NO:2 is encoded by the amino acids from position 1 to 32. Also preferred is such an N-terminal capping module having a glycine or aspartate residue at position 5.

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation. In some embodiments, the target is VEGF-Axxx or VEGFR-2.

The term "consensus sequence" refers to an amino acid sequence, wherein the consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. The two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in the two or more repeat units, the consensus amino acid may be one of the most frequently found amino acids or a combination of the two or more amino acid residues.

In one embodiment, one may also use non-naturally occurring binding proteins or binding domains.

The term "non-naturally occurring" means synthetic or not from nature, for example, made by a person. The term "non-naturally occurring binding protein" or "non-naturally occurring binding domain" means that the binding protein or the binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of the binding protein or the binding domain is not present as a non-artificial sequence entry in a sequence database, for example in GenBank, EMBL-Bank or Swiss-Prot. These databases and other similar sequence databases are well known to the person skilled in the art.

A binding domain can inhibit VEGF-Axxx binding to VEGFR-2 either by binding to VEGF-Axxx or by binding to VEGFR-2 in a way that the apparent dissociation constant ($K_d$) between VEGF-Axxx and VEGFR-2 is increased more than $10^2$-fold. In other embodiments, the dissociation constant is increased more than $10^3$-fold, more than $10^4$-fold, more than $10^5$-fold, or more than $10^6$-fold. In one embodiment, the $K_d$ for the interaction of the binding domain to either VEGF-Axxx or VEGFR-2 is below $10^7$M, below $10^8$M, or below $10^9$M, below $10^{10}$M, or below $10^{11}$M. Methods to determine dissociation constants of protein-protein interactions, such as surface plasmon resonance (SPR) based technologies, are well known to the person skilled in the art.

The binding domain binds VEGF-Axxx. In one embodiment, the binding domain binds human VEGF-A165. In other embodiments, it may bind other VEGF-A isoforms.

In one embodiment, the binding protein and/or binding domain do not lose their native three-dimensional structure upon incubation in PBS containing 100 mM dithiothreitol (DTT) for 1 or 10 hours at 37° C. "PBS," as used here, means a phosphate buffered water solution containing 137 mM NaCl, 10 mM phosphate and 2.7 mM KCl and having a pH of 7.4.

In one embodiment, the binding protein comprises a binding domain that inhibits VEGF-Axxx binding to VEGFR-2 and has the midpoint denaturation temperature and non-aggregating properties as defined above, wherein the binding protein inhibits sprouting of HUVEC spheroids with an $IC_{50}$ value below 100 nM.

The term "HUVEC" means human umbilical vein endothelial cells, which can be isolated from normal human umbilical vein and which are responsive to VEGF-A stimulation.

Assays to measure the sprouting of HUVEC spheroids are well known to the person skilled in the art.

An $IC_{50}$ value is the concentration of a substance, such as a binding protein or binding domain, which is required for 50% inhibition in vitro of an experimental determined parameter, such as the sprouting of HUVEC spheroids. $IC_5 0$ values can be readily determined by the person skilled in the art (Korff T. and Augustin H. G., J. Cell Biol. 143(5), 1341-52, 1998).

In one embodiment, the binding protein and/or binding domain inhibit the sprouting of HUVEC spheroid with an $IC_{50}$ value below 10 nM, below 1 nM, below 0.1 nM, or below 0.05 nM.

In another embodiment, one can use a monomeric binding protein and/or binding domain that inhibit the sprouting of HUVEC spheroids with an $IC_{50}$ value lower than the corresponding $IC_{50}$ value of ranibizumab, bevacizumab, aflibercept, or pegaptanib.

In one embodiment, the $K_d$ for the interaction of a binding domain to VEGF-B, VEGF-C, VEGF-D, PlGF or PDGF is above 1 nM, above 10 nM, above $10^2$ nM, above $10^3$ nM, or above $10^4$ nM.

In one embodiment, VEGF-Axxx is either dog VEGF-A 164 or simian VEGF-A 165 or human VEGF-A165, and VEGF-Axxxb is either dog VEGF-A 164b or simian VEGF-A165b or human VEGF-A165b.

Another embodiment is a recombinant binding protein comprising a binding domain, wherein the binding domain inhibits VEGF-Axxx binding to VEGFR-2 and wherein the binding domain is a repeat domain or a designed repeat domain. Such a repeat domain may comprise one, two, three or more internal repeat modules that will participate in binding to VEGF-Axxx. In one embodiment, such a repeat domain comprises an N-terminal capping module, two to four internal repeat modules, and a C-terminal capping module. In one embodiment, the binding domain is an ankyrin repeat domain or designed ankyrin repeat domain.

In one embodiment the binding protein comprises a binding domain as described herein, conjugated to a polyethylene glycol (PEG) moiety. In one embodiment the PEG moiety is coupled to a single Cys residue of the binding domain. The Cys residue can be genetically introduced at the C-terminal end of the binding domain. The PEG moiety can then be coupled by chemical means, for example, by using maleimide chemistry well known to the person skilled in the art.

Another embodiment is a recombinant binding protein as defined above comprising at least one repeat domain with binding specificity for VEGF-Axxx, wherein the repeat domain competes for binding to VEGF-Axxx with a repeat domain selected from the group of the repeat domains of SEQ ID NO:1 to 7. In one embodiment, the repeat domain competes for binding to VEGF-Axxx with the repeat domain of SEQ ID NO:1 or 3. In another embodiment, the repeat domain competes for binding to VEGF-Axxx with the repeat domain of SEQ ID NO:3.

The term "compete for binding" means the inability of two different binding domains of the invention to bind simultaneously to the same target, while both are able to bind the same target individually. Thus, such two binding domains compete for binding to the target. Methods, such as competition ELISA or competition SPR measurements (e.g. by using the Proteon instrument from BioRad), to determine if two binding domains compete for binding to a target are well known to the practitioner in the art.

A recombinant binding protein that competes for binding to VEGF-Axxx with a selected repeat protein can be identified by methods well know to the person skilled in the art, such as a competition Enzyme-Linked Immunosorbent Assay (ELISA).

Another embodiment is a recombinant binding protein comprising a repeat domain with binding specificity for VEGF-Axxx selected from the group consisting of the repeat domains of SEQ ID NO:1 to 7. In one embodiment, the repeat domain is selected from the repeat domains of SEQ ID NO:2 or 3. In another embodiment, the repeat domain is the repeat domain of SEQ ID NO:3.

One or more polyethylene glycol moieties may be attached at different positions in the binding protein, and such attachment may be achieved by reaction with amines, thiols or other suitable reactive groups. Attachment of polyethylene glycol moieties (PEGylation) may be site-directed, wherein a suitable reactive group is introduced into the protein to create a site where PEGylation preferentially occurs, or is originally present in the binding protein. The thiol group may be present in a cysteine residue; and the amine group may be, for example, a primary amine found at the N-terminus of the polypeptide or an amine group present in the side chain of an amino acid, such as lysine or arginine. In one embodiment, the binding protein is modified so as to have a cysteine residue at a desired position, permitting site directed PEGylation on the cysteine, for example by reaction with a polyethylene glycol derivative carrying a maleimide function. The polyethylene glycol moiety may vary widely in molecular weight (i.e. from about 1 kDa to about 100 kDa) and may be branched or linear. In one embodiment, the polyethylene glycol has a molecular weight of about 1 to about 50 kDa; in another embodiment, the polyethylene glycol has a molecular weight of about 10 kDa to about 40 kDa, about 15 kDa to about 30 kDa, or about 20 kDa. Examples of such binding proteins and methods for synthesizing them are provided in WO 2011/135067, the entire contents of which are incorporated herein by reference.

In one embodiment, one can use a recombinant protein comprising a binding domain as described herein, wherein the recombinant protein is conjugated at its C-terminal cysteine thiol to a maleimide-coupled PEG, such as α-[3-(3-maleimido-1-oxopropyl)amino]propyl-ω-methoxy-polyoxyethylene (NOF, Sunbright ME-200MA (20 kD) or Sunbright ME-400MA (40 kD)). In one embodiment, one can use a recombinant binding protein comprising a binding domain as described herein, wherein the binding domain is conjugated at its C-terminus via a peptide bond to SEQ ID NO:8, which is in turn conjugated at the C-terminal cysteine thiol to a maleimide-coupled PEG, such as α-[3-(3-maleimido-1-oxopropyl)amino]propyl-ω-methoxy-polyoxyethylene (NOF, Sunbright ME-200MA (20 kD) or Sunbright ME-400MA (40 kD)).

In some embodiments, the C-terminal cysteine thiol can be conjugated to a pyridyl disulfide-coupled PEG, a vinyl sulfone-coupled PEG, or a PEG coupled via other thiol reagent.

In some embodiments, the PEG and appropriate linking compound has a molecular weight of at least about 2 kD, 5 kD, 10 kD, 20 kD, 30 kD, 40 kD, 50 kD, 70 kD, or 100 kD. In one embodiment the maleimide-coupled PEG has a molecular weight of at least about 2 kD, 5 kD, 10 kD, 20 kD, 30 kD, 40 kD, 50 kD, 70 kD, or 100 kD.

In certain embodiments the α-[3-(3-maleimido-1-oxopropyl)amino]propyl-ω-methoxy-polyoxyethylene has a molecular weight of at least about 20 kD or at least about 40 kD.

In some embodiments, a recombinant binding protein can be conjugated at a N-terminal amino group to a suitable PEG-containing linking compound. In such embodiments, PEG-ethylene reagents, PEG NHS-esters, PEG NHS-carbonate, PEG-p-nitrophenyl carbonates, PEG-triazine reagents, and the like may be conjugated at the N-terminus of a suitable binding protein described herein.

In a further embodiment, the invention relates to nucleic acid molecules encoding the particular recombinant binding proteins. Further, a vector comprising the nucleic acid molecule is considered.

Further, a pharmaceutical composition comprising one or more of the above mentioned binding proteins, in particular recombinant binding proteins comprising repeat domains, or nucleic acid molecules encoding the particular recombinant binding proteins, and optionally a pharmaceutical acceptable carrier and/or diluent is considered.

Formulation

Pharmaceutical acceptable carriers and/or diluents are known to the person skilled in the art and are explained in more detail below. Even further, a diagnostic composition comprising one or more of the above mentioned recombinant binding proteins, in particular binding proteins comprising repeat domains, is considered.

A pharmaceutical composition comprises binding proteins as described above and a pharmaceutically acceptable carrier, excipient or stabilizer (Remington's Pharmaceutical Sciences 16th edition, Osol, A. Ed. [1980]). Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anticancer agent or an anti-angiogenic agent (for example human VEGF-Axxxb; preferably, human VEGF-A165b).

In one embodiment, a formulation comprises binding proteins as described above and a detergent such as nonionic detergent, including but not limited to polysorbate 20 (e.g. about 0.04%), a buffer such as histidine, phosphate or lactic acid and a sugar such as sucrose or trehalose. The formulation may also comprise PBS.

The formulations to be used for in vivo administration must be aseptic or sterile. This is readily accomplished by filtration through sterile filtration membranes.

Methods of Treatment

In one embodiment, the method of the invention comprises a method of inhibiting binding between VEGF-Axxx and VEGFR-2 by administering to a patient in need of such inhibition, at a frequency between every 8 weeks and every 16 weeks, a dose of about 2 mg to about 4 mg of a recombinant binding protein comprising an ankyrin repeat domain, wherein the ankyrin repeat domain is selected from the group consisting of the ankyrin repeat domains of SEQ ID NOS:1 to 7. In some embodiments, the ankyrin repeat domain is selected from the group consisting of the ankyrin repeat domains of SEQ ID NOS:1 to 5. In some embodiments, the ankyrin repeat domain is selected from the group consisting of the ankyrin repeat domains of SEQ ID NOS: 2 or 3. The methods can be used to treat certain ocular conditions, including those related to ischemic retinopathy, neovascular retinopathy, or both ischemic retinopathy and neovascular retinopathy. Some conditions related to ischemic retinopathy, that can be treated by methods disclosed herein, can include diabetic macular edema, central vein occlusion, and branched vein occlusion. Some conditions related to neovascular retinopathy, that can be treated by methods disclosed herein, can include proliferative diabetic retinopathy, exudative age-related macular degeneration, pathological myopia, choroidal neovascularation, secondary to histoplasmosis, polypoidal choroidal neovasularization, and retinal angiomatous proliferation, The method may be used to treat age-related macular degeneration, diabetic macular edema, pathological myopia branch retinal vein occlusion, and central retinal vein occlusion. The method may also be used to treat patients have the above-listed diseases who are refractory to existing anti-VEGF therapies.

To "treat," as used here, means to deal with medically. It includes, for example, administering the recombinant binding protein of the invention to prevent the onset of AMD as well as to alleviate its severity.

In one embodiment, the binding protein is administered every 8 weeks. In another embodiment, the binding protein is administered every 9 weeks, 10 weeks, 11 weeks, 12 weeks, 13 weeks, 14 weeks, 15 weeks, or 16 weeks. In one embodiment, the binding protein is administered every 8 weeks to 10 weeks, every 10 weeks to 12 weeks, every 12 weeks to 14 weeks, or every 14 weeks to 16 weeks. In another embodiment, the binding protein is administered every 4 weeks to 12 weeks, or every 8 weeks to 12 weeks, or every 12 weeks to 16 weeks. In some embodiments, the protein is administered at one or more of the frequencies described above for the remainder of the lifetime of the patient.

Macular degeneration results from the neovascular growth of the choroid vessel underneath the macula. There are two types of advanced macular degeneration: exudative and atrophic. While exudative macular degeneration only comprises 15% of all macular degeneration, nearly all exudative macular degeneration leads to blindness. Once one eye is affected by exudative macular degeneration, the condition almost always affects the other eye. Exudative and atrophic macular degeneration are often called age-related macular degeneration or age-related "wet" macular degeneration as the diseases are found mostly in elderly persons.

As used here, "refractory to anti-VEGF therapy" refers to the inability to achieve a satisfactory physiological response with known anti-VEGF therapy, such as ranibizumab, bevacizumab, aflibercept, or pegaptanib therapy. Such patients have less than a 20% decrease in abnormal central retina thickness (center 1 $mm^2$ area of the macula) after 3 intravitreal injections of ranibizumab, bevacizumab, or aflibercept (or 3 intravitreal injections of a combination of any of the foregoing therapies). In one embodiment, a patient who is refractory to anti-VEGF therapy experiences a continuing worsening of vision despite ranibizumab, bevacizumab, aflibercept, or pegaptanib therapy. In another embodiment, a patient who is refractory to anti-VEGF therapy experiences thickening of the retina despite ranibizumab, bevacizumab, aflibercept, or pegaptanib therapy. In some embodiments, patients refractory to anti-VEGF therapy demonstrate negligible anatomical improvement despite receiving ranibizumab, bevacizumab, aflibercept, or pegaptanib therapy.

In some embodiments, the binding proteins are administered intravitreally at a dose between 0.1 mg and 10 mg of binding proteins per injection, between 0.3 mg and 6 mg of binding proteins per injection, or between 1 mg and 4 mg per injection. In some embodiments, the binding proteins are administered at a dose containing between 0.5 mg and 5 mg of binding proteins per injection, between 1.0 mg and 4.0 mg of binding proteins per injection, between 2.0 mg and 4.0 mg of binding proteins per injection, or between 3.0 mg and 4.0 mg of binding proteins per injection. In an embodiment, the binding proteins are administered at a dose of 2 mg of binding proteins per injection. In another embodiment, the proteins are administered at a dose of 3 mg of binding proteins per injection.

According to some embodiments, a patient receiving injections of recombinant binding proteins disclosed herein every four weeks to sixteen weeks can demonstrate a 20% or greater reduction in abnormal central retina thickness from baseline. According to some embodiments, a patient receiving injections of recombinant binding proteins disclosed herein every eight weeks to twelve weeks can demonstrate a 20% or greater reduction in abnormal central retina thickness from baseline. According to some embodiments a patient receiving injections of recombinant binding proteins disclosed herein can demonstrate a 30% or greater reduction in abnormal central retina thickness from baseline. According to yet other embodiments a patient receiving injections of recombinant binding proteins disclosed herein can demonstrate a 40% or greater reduction in abnormal central retina thickness from baseline.

According to some embodiments, a patient, who is refractory to Anti-VEGF treatments such as anibizumab, bevacizumab, aflibercept, or pegaptanib, after receiving one or more injections of binding proteins disclosed herein can demonstrate about a 20% or greater reduction in abnormal central retina thickness from baseline. According to some embodiments a patient after receiving one or more injections of binding proteins disclosed herein can demonstrate about a 30% or greater reduction in abnormal central retina thickness from baseline. According to yet other embodiments a patient after receiving one or more injections of binding proteins disclosed herein can demonstrate less than a 40% or greater reduction in abnormal central retina thickness from baseline.

For example, a method for the treatment of an ocular condition, such as age-related macular degeneration can include an intravitreal injection of a recombinant binding protein in an amount in the range of 0.5 mg to 5 mg once every twelve weeks to once every sixteen weeks. The recombinant binding protein can include an ankyrin repeat domain, wherein the ankyrin repeat domain is selected from the group consisting of the ankyrin repeat domains of SEQ ID NO: 3.

In another example, a method for the treatment of age-related macular degeneration in a patient who is refractory to an anti-VEGF treatment such as ranibizumab, bevacizumab, or ranibizumab and bevacizumab, can include an intravitreal injection of a recombinant binding protein in an amount in the range of 0.5 mg to 5 mg. The recombinant binding protein can include an ankyrin repeat domain, wherein the ankyrin repeat domain is selected from the group consisting of the ankyrin repeat domains of SEQ ID NO: 3. In such an example, a patient receiving such injection or injections can experience more than a 20% decrease in abnormal central retina thickness after receiving one or more injections. In some embodiments, a patient receiving such injection or injections does not experience a thickening of the retina after receiving one or more injections.

In another example, a method for the treatment of diabetic macular edema in a patient who is refractory to an anti-VEGF treatment such as ranibizumab, bevacizumab, or ranibizumab and bevacizumab, can include an intravitreal injection of a recombinant binding protein in an amount in the range of 0.5 mg to 5 mg. The recombinant binding protein can include an ankyrin repeat domain, wherein the ankyrin repeat domain is selected from the group consisting of the ankyrin repeat domains of SEQ ID NO: 3. In such an example, a patient receiving such injection or injections can experience more than a 20% decrease in abnormal central retina thickness after receiving one or more injections. In some embodiments, a patient receiving such injection or injections does not experience a thickening of the retina after receiving one or more injections.

EXAMPLES

Example 1

Treatment of Patients Refractory to Existing Treatments

Figures 2A, 2B:
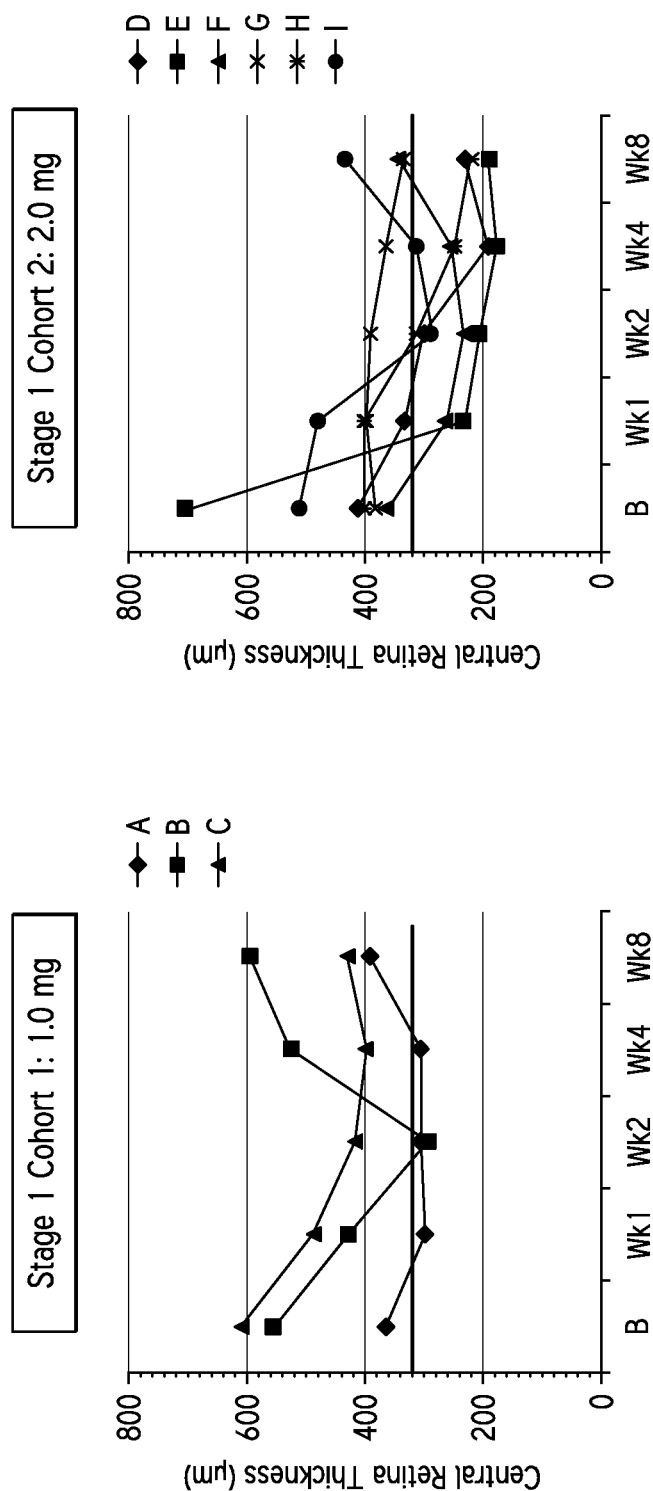
FIG. 2a shows central retina thickness in human patients, refractory to LUCENTIS® and/or AVASTIN® therapy, after receiving 1.0 mg of a composition according to the invention comprising the ankyrin repeat domains of SEQ ID NO: 3. The composition was dissolved in PBS and administered via intravitreal injection in a 50 µl volume.
FIG. 2b shows central retina thickness in human patients, refractory to LUCENTIS® and/or AVASTIN® therapy, after receiving 2.0 mg of a composition according to the invention comprising the ankyrin repeat domains of SEQ ID NO: 3. The composition was dissolved in PBS and administered via intravitreal injection in a 50 µl volume.

Several patients suffering from age-related macular degeneration who were refractory to ranibizumab (LUCENTIS®) or bevacizumab (AVASTIN®) therapy were treated via injection of a composition according to the invention comprising the ankyrin repeat domains of SEQ ID NO: 3. The compositions were all dissolved in PBS and administered via intravitreal injection in a 50 µl to 70 µl volume Three patients received 1.0 mg injections of the composition dissolved in PBS and administered via intravitreal injection in a 50 µl volume, the retinal thicknesses of the patients receiving the injections over time are shown in FIG. 2a. The patients' retinal thicknesses were determined using spectral domain optical coherence tomography ("OCT"). These patients were refractive to existing VEGF therapies.

As illustrated in FIG. 2a, patients A and C surprisingly demonstrated a cumulative reduction in central retinal thickness from baseline after receiving an injection of a composition including 1.0 mg of recombinant binding proteins including the ankyrin repeat domains of SEQ ID NO: 3, over a length of time of eight weeks. As is seen in the figure, patients A, B, and C all surprisingly demonstrated a cumulative reduction in central retinal thickness from baseline after receiving an injection of a composition including recombinant binding proteins including the ankyrin repeat domains of SEQ ID NO: 3, over a length of time of two weeks.

Six patients received 2.0 mg injections of the composition dissolved in PBS and administered via intravitreal injection in a 50 µl volume, the retinal thicknesses of the patients receiving the injections over time are shown in FIG. 2b. The patients' retinal thicknesses were determined using OCT. These patients were refractive to existing VEGF therapies.

As illustrated in FIG. 2b, patients D, E, F, G, H and I surprisingly demonstrated a cumulative reduction in retinal thickness from baseline after receiving an injection of a composition including 2.0 mg of recombinant binding proteins including the ankyrin repeat domains of SEQ ID NO: 3, over a length of time of eight weeks.

Six patients received 3.0 mg injections of the composition dissolved in PBS and administered via intravitreal injection in a 50 µl volume, the retinal thicknesses of the patients receiving the injections over time are shown in FIG. 3a. The patients' retinal thicknesses were determined using OCT. These patients were refractive to existing VEGF therapies.

As illustrated in FIG. 3a, patients J, K, M, N, and O surprisingly demonstrated a cumulative reduction in retinal thickness from baseline after receiving an injection of a composition including 3.0 mg of recombinant binding proteins including the ankyrin repeat domains of SEQ ID NO: 3, over a length of time of eight weeks. As is seen in the figure, patients J, K, L, M, N, and O all surprisingly demonstrated a cumulative reduction in retinal thickness from baseline after receiving an injection of a composition including recombinant binding proteins including the ankyrin repeat domains of SEQ ID NO: 3, over a length of time of four weeks.

Nine patients received 4.2 mg injections of the composition dissolved in PBS and administered via intravitreal injection in a 50 µl volume, the retinal thicknesses of the patients receiving the injections over time are shown in FIG. 3b. The patients' retinal thicknesses were determined using OCT. These patients were refractive to existing VEGF therapies.

As illustrated in FIG. 3b, patients S, U, and V surprisingly demonstrated a cumulative reduction in retinal thickness from baseline after receiving an injection of a composition according to the invention including 4.2 mg of recombinant binding proteins including the ankyrin repeat domains of SEQ ID NO: 3, over a length of time of sixteen weeks. As is seen in the figure, patients S, U, V, and X surprisingly demonstrated a cumulative reduction in retinal thickness from baseline after receiving an injection of a composition according to the invention including 4.2 mg of recombinant binding proteins including the ankyrin repeat domains of SEQ ID NO: 3, over a length of time of twelve weeks. As is seen in the figure, patients P, S, U, V, and X all surprisingly demonstrated a cumulative reduction in retinal thickness from baseline after receiving an injection of a composition including 4.2 mg recombinant binding proteins including the ankyrin repeat domains of SEQ ID NO: 3, over a length of time of eight weeks.

Example 2

Duration of Treatment Effect

Figure 4:
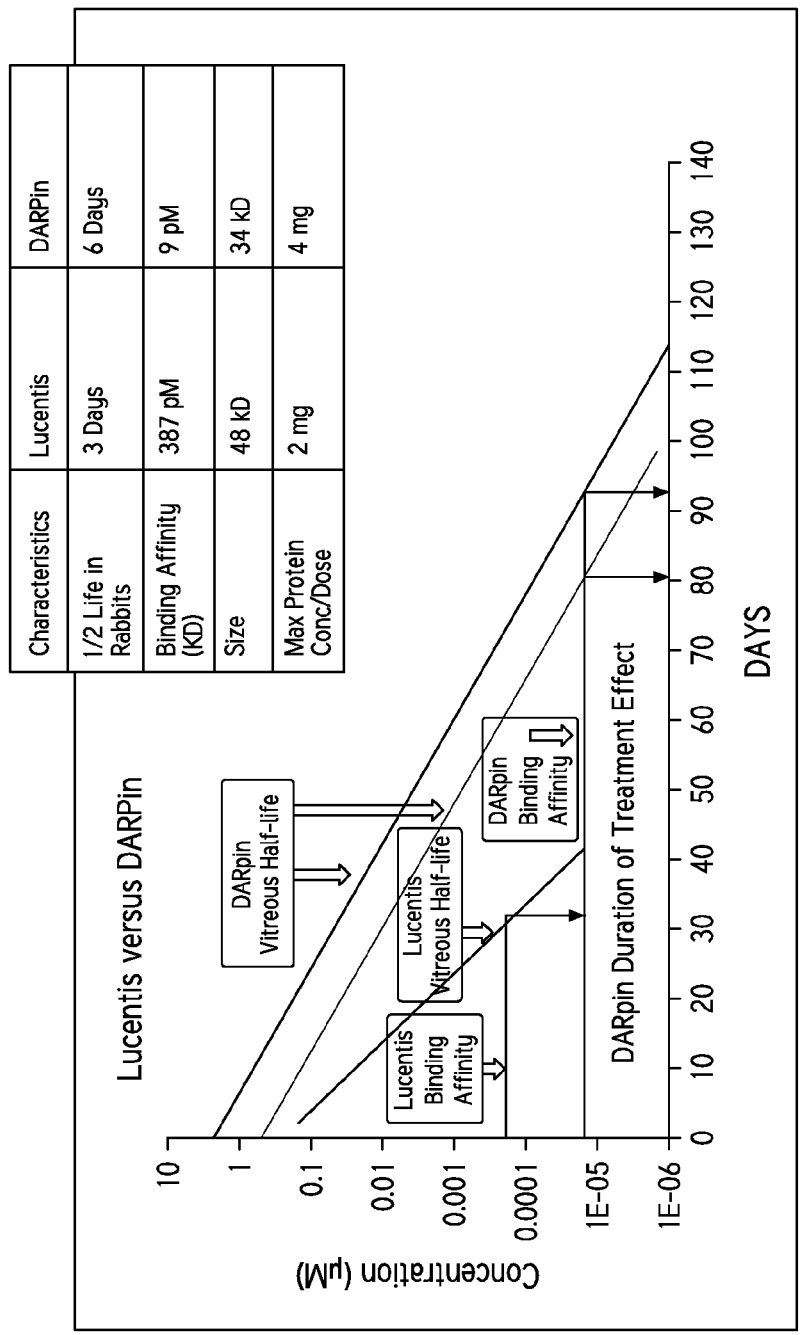
FIG. 4 illustrates duration of treatment effect of an example embodiment of the compositions disclosed herein compared to ranibizumab (Commercially available as LUCENTIS®).

FIG. 4 is a diagram that describes that binding affinity and vitreous half-life define the duration of effect of a VEGF inhibitor. The figure describes the half life and duration of treatment effect of two different dosage concentrations of recombinant binding proteins according to the disclosure herein (referred to as "DARPin") as compared to ranibizumab (LUCENTIS®). As is illustrated in FIG. 4, both DARPin dosages demonstrate a longer half life and longer duration of treatment effect as compared to ranibizumab.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition while the number of variations have been shown and described in detail, other modifications, which are within the scope of this invention, will be readily apparent to those of skill in the art based on this disclosure. It is also contemplated that various combinations or subcombinations of the specific features and aspects of the embodiments can be made and still fall within the scope. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A method of treating age-related macular degeneration, the method comprising the step of administering to a patient in need of such treatment, at a frequency of 8 weeks, a dose of about 2 mg of a recombinant binding protein comprising SEQ ID NO: 3, wherein the patient experiences continuing worsening of vision despite ranibizumab, bevacizumab, aflibercept, and pegaptanib therapy.

2. The method of claim 1, wherein the binding protein further comprises a polyethylene glycol moiety of at least 5 kDa molecular weight.

3. The method of claim 2, wherein the binding protein comprises an ankyrin repeat domain conjugated at its C-terminus via a peptide bond to a polypeptide linker and a C-terminal Cys residue, wherein the thiol of the C-terminal Cys is further conjugated to a maleimide-coupled polyethylene glycol.

4. The method of claim 3, wherein the polyethylene glycol moiety has a molecular weight of around 20 kDa.

5. The method of claim 4, wherein the maleimide-coupled polyethylene glycol is α-[3-[3-maleimido-l-oxopropyl) aminopropyl-w-methoxy-polyoxyethylene, and wherein the polyethylene glycol moiety has a molecular weight of at least 10 kDa.

6. The method of claim 1, wherein the patient has less than a 20% decrease in the center 1 mm$^2$ area of the macula after 3 intravitreal injections of ranbizumab, bevacizumab, or aflibercept.

* * * * *